United States Patent [19]

Runge et al.

[11] Patent Number: 4,615,879

[45] Date of Patent: Oct. 7, 1986

[54] PARTICULATE NMR CONTRAST AGENTS FOR GASTROINTESTINAL APPLICATION

[75] Inventors: Val M. Runge; Jeffrey A. Clanton, both of Nashville, Tenn.

[73] Assignee: Vanderbilt University, Nashville, Tenn.

[21] Appl. No.: 551,003

[22] Filed: Nov. 14, 1983

[51] Int. Cl.$^4$ .................. A61K 49/00; A61B 5/05; A61B 6/00

[52] U.S. Cl. ........................ 424/9; 128/653; 128/654; 424/4; 436/173; 436/806

[58] Field of Search ............ 436/173; 128/653, 654; 424/2, 4, 9

[56] References Cited

U.S. PATENT DOCUMENTS 4,352,751 10/1982 Wieder et al. .............. 435/4 X

FOREIGN PATENT DOCUMENTS 8633082 1/1983 Australia .................... 424/9
0071564 2/1983 European Pat. Off. ....... 424/9

OTHER PUBLICATIONS

Runge et al., Radiology, vol. 147, (1983), pp. 789-791.
Wesbey et al., Radiology, vol. 149, (1983), pp. 175-180.
U.S.P. XVI, (The United States Pharmacopeia), 1960, pp. 1072-1073.
Young et al., CT, 5:543-546 (1981).
U.S.P. XX, p. 1105.
Newhouse et al., Radiology, 142:246 (1982).
Mansfield and Morris, "NMR Imaging in Biomedicine", Supp. 2, Chap. 7, pp. 217-245; and Notes Added in Proof (1982, Academic Press).

*Primary Examiner*—Christine M. Nucker
*Assistant Examiner*—Stephen C. Wieder
*Attorney, Agent, or Firm*—Tilton, Fallon, Lungmus & Chestnut

[57] ABSTRACT

Contrast media compositions for nuclear magnetic resonance (NMR) imaging of the gastrointestinal system are provided for oral or rectal administration. The compositions comprise aqueous suspensions of particles of an NMR contrast agent, the particles being very finely-divided and providing in their outer surfaces a substantially water-insoluble paramagnetic compound. Suspending and/or wetting agents may be included to maintain the contrast agent particles in a dispersed, suspended condition for the oral or rectal administration. Buffering agents may also be included to maintain the pH of the suspension in a pH range protecting the insolubility of the paramagnetic compound.

12 Claims, No Drawings

PARTICULATE NMR CONTRAST AGENTS FOR GASTROINTESTINAL APPLICATION

FIELD OF THE INVENTION

The field of the invention is that of nuclear magnetic resonance (NMR) imaging for diagnostic examination of the body, and the contrast agents used to enhance the NMR image. In particular, this invention is concerned with contrast agents which may be administered either orally or rectally for examination of the gastrointestinal system.

BACKGROUND AND PRIOR ART

Oral and rectal contrast agents for identification of the gastrointestinal tract are needed in NMR imaging. In the search for intraabdominal disease, fluid or feces filled loops of bowel must be distinguished from inflammatory or neoplastic disease, which may also present as mass lesions. In pancreatic imaging, the c-loop of the duodenum must be visualized in order to identify the pancreatic head.

By opacification of the c-loop of the duodenum, the location of the pancreatic head may be determined and differentiated from surrounding soft tissue. In NMR, like CT, soft tissue masses in the abdomen are difficult to distinguish from fluid or feces filled bowel loops. This discrimination could be made with the use of a safe, effective contrast agent. This would enable the diagnosis by NMR imaging of intraabdominal abscesses or neoplastic tissue masses.

Barium sulfate and the iodinated contrast agents used in conventional radiology do not cause a marked change consistently in proton density, $T_1$ or $T_2$, in patient examinations necessitating attempts to find new agents. Mineral oil may be used to opacify bowel loops on NMR imaging, increasing the proton density signal. Newhouse et al, Radiology 142: 246 (1982). However, administration of sufficient quantities may be hazardous to the patient. Ferric chloride has been tried experimentally to enhance spin-lattice relaxation ($T_1$) and allow visualization of the stomach. Young et al, *J. Comp. Tomo.* 5: 543–546 (1981). Absorption of iron with associated acute symptomatology prevents widespread clinical application of this approach.

SUMMARY OF INVENTION

A contrast agent by definition must produce a significant change in the signal being observed. A large change in signal intensity, provided by a relatively small quantity of compound, is desired. These characteristics can produce a consistent observable change which increases the diagnostic information available from radiological procedures. For example, barium sulfate and iodinated compounds absorb X-rays and thus act as effective contrast agents in both conventional radiology and X-ray computed tomography (CT). The use of these agents cannot, however, be extended to nuclear magnetic resonance (NMR) imaging. The four parameters measurable by NMR, proton density, $T_1$, $T_2$, and flow, are not greatly influenced by the presence of barium or iodine. Paramagnetic compounds can enhance proton relaxation in NMR imaging. This enhancement of relaxation, which is equivalently described as a reduction in the spin-lattice ($T_1$) and/or spin-spin ($T_2$) relaxation times, is produced by the interaction of unpaired electrons from the paramagnetic species with the hydrogen nuclei of water.

Heretofore NMR contrast agents have been administered, (viz. intravenously or orally) in the form of water-soluble paramagnetic compounds. However, paramagnetic ions in their free ion form are generally toxic. The most effective paramagnetic metals such as gadolinium or chromium, are highly toxic as free ions at the concentrations needed for effective NMR imaging. Consequently, for intravenous administration it has been proposed that the paramagnetic metal ions can be chelated to reduce their toxicity. (See, for example, the published European Patent Application No. 0 071 564, and/or Australian application 86330-82.). Because the paramagnetic metal ions must interact with the protons of the water, it has been generally believed that effective contrast agents should be in water-soluble form, such as free or chelated ions in solution.

This invention is based on the discovery that water-insoluble paramagnetic compounds can be employed for NMR imaging of the gastrointestinal system when administered either orally or rectally in an aqueous suspension containing finely divided particles of the particulate contrast agent. Because of the substantial insolubility of the compounds in the form administered, the paramagnetic metals are rendered relatively non-toxic and safe for introduction into and passage through the gastrointestinal tract. According to the mechanism of the present invention, the resulting paramagnetic effect as observed is due to the particles in suspension. Any trace amounts of the metal ions that may have dissolved are incidental to the NMR imaging. The contrast agents and method of the invention can therefore be used effectively to effectively achieve discriminating opacification of the gastrointestinal tract.

Although not previously recognized, the experimental observations underlying the present invention have demonstrated that the solid phase undissolved paramagnetic metal ions do sufficiently interact with the protons of the water to achieve proton relaxation by significantly affecting the $T_1$ and/or $T_2$ of the protons. A short $T_1$ and $T_2$ lying outside the range of tissue relaxation times can be satisfactorily achieved provided that the paramagnetic particles are in a very finely divided condition. This provides a large surface area for contact with the water protons when the particles are in aqueous suspension. In this way, a greater number of the solid phase paramagnetic ions interact with water protons at a sufficiently close distance to effect relaxation, even though it is only the metal ions on the outer surfaces of the particles which can contribute to the interaction.

DETAILED DESCRIPTION

The metals which display paramagnetic properties are well known. These include transition metals such as titanium, vanadium, chromium, manganese, iron, cobalt, nickel, and copper; lanthnide metals such as europium and gadolinium; and actinide metals such as protactinium. Such paramagnetic metals are potentially capable of enhancing protein relaxation in NMR imaging. However, these paramagnetic metals if introduced into the gastrointestinal tract in water-soluble form are markedly toxic at concentration levels required for effective NMR imaging. Further, objectionable side effects on the gastrointestinal tract are quite likely. However, the present invention utilizes the paramagnetic metals in substantially water-insoluble forms, such as water-insoluble salts, oxides, or complexes of the metals.

In one embodiment, the suitability of compounds for use in the present invention, such as for oral administration, can be determined by testing the solubility of the compound in the finely divided condition in which it is to be administered in aqueous hydrochloric acid, thereby simulating the gastric fluid of the stomach. For example, it can be determined that the paramagnetic compound is insoluble at least to the extent that less than 1% by weight (in the particulate form to be administered) dissolves in 30 minutes at a temperature of 37° C. in water adjusted to a pH of 1.2 with hydrochloric acid. The concentration used and the degree of agitation are not particularly critical. However, for uniformity five parts by weight of the paramagnetic compound may be used per 100 parts of aqueous hydrochloric acid, and the mixture may be subjected to mild agitation for the 30 minutes of the test. The test criteria is particular application to compounds of the most highly toxic paramagnetic metals, a number of which exhibit the greatest effect on NMR imaging. These metals include gadolinium and chromium.

The foregoing solubility test is related to the simulated gastric fluid prepared as described in U.S.P. XX, page 1105. According to the procedure there described 2.0 g of sodium chloride and 3.2 g of pepsin and 7 ml of hydrochloric acid are combined with sufficient water to make 1000 ml. The resulting test solution has a pH of about 1.2. If desired, a solubility test with the particulate paramagnetic compound may be conducted using the U.S.P. simulated gastric fluid and the conditions described above.

As a further test for insolubility if required, the particulate paramagnetic compound may be subjected to the simulated intestinal fluid described in U.S.P. XX, page 1105. The conditions of the test may be the same as described above for the pH 1.2 aqueous HCl. However, if the fine particles of the paramagnetic compound are sufficiently insoluble according to the standard defined above in aqueous hydrochloric acid, it may be assumed that the compound is sufficiently insoluble for rectal as well as for oral administration, even though no other precautions are taken to maintain insolubility during passage through the gastrointestinal system.

In another embodiment, which may be used with paramagnetic compounds which are more readily solubilized by acid pH's, the particulate compound may be dispersed in an aqueous buffered solution. The buffer system may be selected to maintain a pH at which the compound remains insoluble, for example, an approximately neutral or weakly alkaline pH (viz. 6.0 to 8.5). The suitability of the buffered suspension, may be tested in the same manner as described above, that is, by determining that no more than 1% by weight of the paramagnetic compound dissolves in 30 minutes in the aqueous buffer at 37° C. (the pH being that of the buffered solution). Examples of suitable physiologically acceptable buffers are: (1) Magnesia and Alumina Oral Suspension USP, a mixture containing 3.4 to 4.2% magnesium hydroxide and aluminum hydroxide with hydrated aluminum oxide equivalent to 2.0 to 2.4% aluminum oxide; (2) an aqueous solution of bicarbonate; such as sodium or potassium bicarbonate USP; and (3) an aqueous solution of a phosphate buffer, such as a mixture of mono- and di-potassium phosphate. The Magnesia and Alumina Suspension can also function as a suspending agent. The buffered pH will be slightly alkaline (e.g. pH 8.3). With the bicarbonate buffer a slightly alkaline pH can be obtained (e.g. pH 7.5), and with the phosphate buffer, an approximately neutral pH. Such buffer systems can be used with any of the paramagnetic compounds but are particularly suitable for use with paramagnetic metals having a relatively low degree of toxicity such as the iron compounds. With iron compounds some degree of solubilization in the digestive tract could be accepted. Following the NMR imaging the administered dispersion can be diluted by administering aqueous fluids, either orally or rectally, and enemas or laxatives can be used to decrease the residence time of the paramagnetic metals, and to limit the absorption into the circulatory system of any of the metal which has been solubilized.

Examples of compounds which have been found to be suitable for use in practicing this invention are: gadolinium oxalate, chromium acetylacetonate (Cr tris acac), and iron sulfide. Other illustrative examples of paramagnetic compounds which may be used in solid particulate form include:

Iron(II) carbonate (siderite), $FeCO_3$
Iron silicide, $FeSi$
Iron diphosphide, $Fe_2P$
Iron disulfide (Morcasite), $FeS_2$
Chromium mononitride, $CrN$
$Gd_2(C_2O_4)_3.10H_2O$, Gd (III) oxalate
$Gd(CH(COCH_3)_2)_3.3H_2O$, Gd(III) acetylacetonate trihydrate
Copper(II) oleate, $Cu(C_{18}H_{33}O_2)_2$
Copper xanthate, $Cu(C_3H_5OS_2)_2$ Water-insoluble compounds of gadolinium, chromium, and iron are believed to be the most advantageous for the purposes of this invention. Gadolinium and chromium are among the most highly paramagnetic metals and may therefore be used effectively at lower concentrations, which can contribute to the safety of their use. Iron compounds are in general less toxic and although iron is less paramagnetic than gadolinium or chromium, larger amounts may be safely used including administration in buffered aqueous suspensions as described above. Additional iron compounds which may be used in buffered suspensions include iron pyrophosphate, iron nitride, and iron orthosilicate.

As previously indicated, the water-insoluble paramagnetic compounds should be utilized in finely-divided condition. In general, the particles should be sized in the range, or at least having an average size, below 100 microns diameter. Preferred embodiments utilize the particles in a size range below 10 microns, such as in the range from 0.1 to 3 microns. If desired, particles smaller than 0.1 microns diameter may be employed such as particles in the colloidal size range. Preferably, the particles are rather closely sized, such as by fine grinding and separation by sieving.

For the desired action it is also important that the particulate water-soluble paramagnetic compound be effectively suspended in the aqueous medium used for its administration. Techniques for accomplishing such suspension are known, being similar to those employed in preparing suspensions of barium sulfate particles for oral or rectal administration. In general, the aqueous medium should contain sufficient and effective amounts of suspending and/or wetting agents to maintain the contrast agent particles in a dispersed suspended condition during administration and imaging. Suspending agents that may be employed include methylcellulose, agar, bentonite, gelatin, hydroxypropyl methylcellulose, magnesium aluminum silicate, pectin, etc. Other hydrocolloids or mineral suspending agents may be used which are non-toxic and orally or rectally administerable.

In addition to the suspending agent, it will usually be desirable to utilize a wetting agent. The wetting agent will aid the suspensions, and improve the contacting between the water and the surface of the particles. Commercially available wetting agents which may be used include: Docusate Sodium Monoethanolamine, Nonoxynol 10, Octoxynol 9, Polyoxyethylene 50 Stearate, Polyoxyl 10 Oleyl Ether, Polyoxyl 20 Cetostearyl Ether, Polyoxyl 40 Stearate, Polysorbate 20, 40, 60, 80, or 85, Sorbitan Monolaurate, Sorbitan Monopalmitute, Sorbitan Monostearate, and Tyloxapol.

The concentration of the particulate paramagnetic compound in the aqueous medium may vary from 0.01 to 50 milligrams per milliliter (mg/m) based on the total contrast medium composition, including the water, other ingredients such as the suspending and the wetting agents, and the particulate paramagnetic compound. Based on present information, it is believed that the preferred range for the particulate agent is from about 0.1 to 10 mg per ml of the medium. Within the concentration ranges the total amount administered can be controlled to give effective NMR imaging.

The amounts of the suspending agent and/or wetting agent to be used are not particularly critical provided sufficient amounts are present to maintain the particulate paramagnetic compound in a dispersed suspended condition. during the administration and imaging. In general, concentrations of the suspending agent in the range from about 2 to 30 percent by weight based on the total composition are suitable, and for the wetting agent from about 0.02 to 1.0 percent by weight based on the total composition.

The procedure for combining the ingredients to produce the contrast media compositions is relatively simple. Sterile ion-free water can be used to provide the aqueous phase, and the other ingredients dispersed therein by simple mixing at ordinary room temperatures. No special heating or sequence of addition is needed. However, mild heating and agitation are desirable to promote the formation of the suspension.

The contrast media compositions and their method of use is further illustrated by the following examples.

EXAMPLE I

Contrast media compositions were prepared from: (1) gadolinium oxalate powder (0.1 to 80 micron particles); and (2) chromium acetylacetonate powder (0.1 to 40 micron particles). Tween 80 (polysorbate 80) was used as a wetting agent, and methylcellulose as a suspending agent. The compounding procedure used was to introduce a measured quantity of the particulate contrast agent into a mortar together with sufficient Tween 80 to wet the powder, mixing with a pestle to distribute the liquid through the powder, and then adding a small quantity of the aqueous methylcellulose. After forming the initial suspension, this was added to the balance of the methylcellulose, and mixed to form a uniform suspension. The final compositions contained a range of contrast agent concentrations (2–10 mg/ml) in approximately 9% aqueous methylcellulose. The suspensions were sufficiently stable for storage, but were remixed to assure uniformity prior to administration.

EXAMPLE II $T_1$ and $T_2$ were determined in vitro for suspensions of gadolinium oxalate and chromium acetylacetonate in 25% Cologel ® (Eli Lilly and Company, Indianapolis, Ind.) at 2.5 MHz using a spin-echo pulsed NMR spectrometer. The concentrations were varied from 0 to 50 mg/ml. The particle size ranged from 0.5 to 100 microns for Gd oxalate. TR (the pulse repetition rate) and TE (the echo delay) were varied over a set range, measuring the signal intensity at each point. A least squares fit was then performed to obtain $T_1$ and $T_2$ for the respective experiments. These measurements were repeated 10 times for each suspension to determine a mean and standard deviation for $T_1$ and $T_2$.

NMR imaging was performed with the Aberdeen, Scotland spin-warp 0.04 Tesla (1.7 MHz) resistive system. Scan time was 4 minutes for a 12 mm transverse slice, allowing construction of proton density and calculated $T_1$ images. Suspensions of the two protype agents were prepared to analyze the effects of particle size, concentration of contrast, and composition of suspending agent on the 0.04 T imaging system. NMR imaging of 8 New Zealand rabbits (4 kg average) was performed using the head system coil prior to and following either oral (via a nasogastric tube) or rectal administration of contrast. Anesthesia was supplied by continuous titration with intravenous pentobarbitol. 50–200 cc of 2–10 mg/ml gadolinium oxalate or chromium acetylacetonate suspended in aqueous solution with methylcellulose was utilized to provide opacification of the gastrointestinal system on NMR imaging. The data is reported below in Table A.

Results

As shown by the data of Table A, on NMR spectroscopy in vitro, increasing the concentration of gadolinium oxalate in aqueous suspension led to a decrease in both $T_1$ and $T_2$. Proton relaxation was enhanced. Also, as shown, chromium acetylacetonate in suspension produced an analogous enhancement of relaxation rates.

On NMR imaging at 0.04 Tesla, both gadolinium oxalate and chromium acetylacetonate produced an enhancement in spin-lattice relaxation. By increasing the concentration of either agent, $T_1$ of the suspension could be reduced below 200 msec. The use of a finer particle size preparation caused a greater reduction in $T_1$. When the proportion of suspending agent was decreased, the particulate preparations were observed visually to sediment and on NMR imaging to have a proportionately smaller effect on $T_1$. Barium sulfate in suspension and iodinated X-ray contrast agents (hypaque) in solution did not significantly effect proton relaxation.

Administration of either gadolinium oxalate or chromium acetylacetonate in suspension via a nasogastric tube produced visualization of the rabbits' stomachs on NMR imaging, identified by the low $T_1$ values. Rectal administration enabled visualization of the colon.

TABLE A

| THE EFFECT OF PARTICULATE CONTRAST AGENTS ON $T_1$ AND $T_2$ AT 0.04 TESLA | | |
|---|---|---|
| Concentration (mg/ml) | $T_1$ (sec) | $T_2$ (sec) |
| Gadolinium Oxalate in 25% Cologel & 0.02% Tween 80 | | |
| 0 | 0.964 ± .004 | 0.21 ± .07 |
| 0.05 | 0.699 ± .004 | 0.20 ± .08 |
| 0.5 | 0.425 ± .002 | 0.17 ± .05 |

TABLE A-continued

THE EFFECT OF PARTICULATE CONTRAST AGENTS ON $T_1$ AND $T_2$ AT 0.04 TESLA

| Concentration (mg/ml) | $T_1$ (sec) | $T_2$ (sec) |
|---|---|---|
| 5.0 | 0.335 ± .001 | 0.14 ± .03 |
| 50 | 0.286 ± .002 | 0.11 ± .01 |
| Chromium Tris Acetylacetonate in 25% Cologel & 0.02% Tween 80 | | |
| 0.05 | 0.874 ± .003 | 0.21 ± .07 |
| 0.5 | 0.549 ± .003 | 0.19 ± .06 |
| 5.0 | 0.220 ± .001 | 0.13 ± .03 |
| 50 | 0.216 ± .001 | 0.07 ± .03 |

EXAMPLE III

Iron compounds which are insoluble in water at a neutral or slightly alkaline pH, but which have a solubility in aqueous hydrochloric acid, may be suspended and administered in Magnesia and Alumina Oral Suspension USP having a slightly alkaline pH. Examples of such iron compounds and the concentrations to be used include: iron pyrophosphate, 10–50 mg/ml; iron nitride, 2–25 mg/ml; and iron orthosilicate, 10–50 mg/ml. The particulate iron compounds are added to the suspension as powders and dispersed therein, the particle size of the powders preferably being below 10 microns, such as from 1 to 3 microns average particle diameter.

We claim:

1. A contrast medium composition for nuclear magnetic resonance (NMR) imaging of the gastrointestinal system, comprising an orally or rectally administrable aqueous suspension of particles of an NMR contrast agent said suspension containing wetting and/or suspending agents to maintain said contrast agent particles in a dispersed suspended condition, said particles comprising a substantially water-insoluble compound of a paramagnetic metal, said particles being sized below 10 microns diameter and being capable of passing through the stomach while remaining in particulate form.

2. The composition of claim 1 in which said particles are composed of a compound of a paramagnetic metal selected from the group consisting of gadolinium, chromium, copper, manganese, and iron, said particles being insoluble to the extent that less than 1% by weight dissolves in 30 minutes at a temperature of 37° C. in water adjusted to a pH of 1.2 with hydrochloric acid.

3. The composition of claim 1 in which the suspension contains a buffering agent to maintain the pH of the suspension at a pH of 6.0 to 8.5 for protecting the insolubility of said particles.

4. The composition of claim 1 in which said paramagnetic metal is selected from the group consisting of gadolinium, chromium, and iron.

5. A contrast medium composition for nuclear magnetic resonance (NMR) imaging of the gastrointestinal system, comprising an orally or rectally administrable aqueous suspension of particles of an NMR contrast agent, said suspension containing of wetting and/or suspending agents to maintain said contrast agent particles in a dispersed suspended condition for the administration, said particles being sized in the range below 3 microns diameter and being composed of a compound of a paramagnetic metal, said particles being insoluble to the extent that less than 1% by weight dissolves in 30 minutes at a temperature of 37° C. in water adjusted to a pH of 1.2 with hydrochloric acid so that said particles are capable of passing through the stomach in particulate form.

6. A contrast medium composition for nuclear magnetic resonance (NMR) imaging of the gastrointestinal system, comprising an orally or rectally adminstrable aqueous suspension of finely-divided particles of an NRM contrast agent, said suspension containing wetting and/or suspending agents to maintain said contrast agent particles in a dispersed suspended condition for the administration, said suspension also containing a buffering agent for maintaining the pH of the suspension in a pH range of 6.0 to 8.5 for protecting the insolubility of the contrast agent, said particles being sized below 3 microns diameter and being composed of a compound of a paramagnetic metal, said particles being insoluble in the suspension to the extent that less than 1% by weight dissolves in 30 minutes at a temperature of 37° C. so that said particles are capable of passing through the stomach in particulate form.

7. The composition of claim 6 in which said paramagnetic metal is gadolinium.

8. The composition of claim 6 in which said paramagnetic metal is chromium.

9. The composition of claim 6 in which said paramagnetic metal is iron.

10. The method of nuclear magnetic resonance (NMR) imaging of the gastrointestinal which includes the step of orally or rectally administering to a human subject the contrast medium composition of claim 1 and obtaining an NMR image of a portion of the gastrointestinal tract in which said paramagnetic compound is present in particulate form.

11. The method of nuclear magnetic resonance (NMR) imaging of the gastrointestinal system which includes the step of orally or rectally administering to a human subject the contrast medium composition of claim 6, and obtaining an NMR image of a portion of the gastrointestinal tract in which said paramagnetic compound is present in particulate form.

12. The method of claim 11 in which said paramagnetic metal is iron.

* * * * *

UNITED STATES PATENT AND TRADEMARK OFFICE
CERTIFICATE OF CORRECTION

PATENT NO. : 4,615,879

DATED : October 7, 1986

INVENTOR(S) : Val M. Runge and Jeffrey A. Clanton

It is certified that error appears in the above-identified patent and that said Letters Patent is hereby corrected as shown below:

The following claims are substituted for claims 1 to 12:

1. A contrast medium composition for nuclear magnetic resonance (NMR) imaging of the gastrointestinal system, comprising an orally or rectally administrable aqueous suspension of particles of an NMR paramagnetic contrast agent, said suspension containing wetting and/or suspending agents to maintain said contrast agent particles in a dispersed suspended condition, said particles comprising a substantially water-insoluble metal compound having paramagnetic $T_1$ imaging properties, said particles being sized below 10 microns diameter and being capable of passing through the stomach while remaining in particulate form.

2. The composition of claim 1 in which said particles are composed of a compound of a paramagnetic metal selected from the group consisting of gadolinium, chromium, copper, and manganese, said particles being insoluble to the extent that less than 1% by weight dissolves in 30 minutes at a temperature of $37°C$ in water adjusted to a pH of 1.2 with hydrochloric acid.

3. The composition of claim 1 in which the suspension contains a buffering agent to maintain the pH of the suspension at a pH of 6.0 to 8.5 for protecting the insolubility of said particles.

4. A contrast medium composition for nuclear magnetic resonance (NMR) imaging of the gastrointestinal system, comprising an orally or rectally administrable aqueous suspension of particles of an NMR paramagnetic contrast agent, said suspension containing

UNITED STATES PATENT AND TRADEMARK OFFICE
CERTIFICATE OF CORRECTION

PATENT NO. : 4,615,879

DATED : October 7, 1986

INVENTOR(S) : Val M. Runge and Jeffrey A. Clanton

It is certified that error appears in the above-identified patent and that said Letters Patent is hereby corrected as shown below:

wetting and/or suspending agents to maintain said contrast agent particles in a dispersed suspended condition for the administration, said particles being sized in the range below 3 microns diameter and being composed of a metal compound having paramagnetic $T_1$ imaging properties, said particles being insoluble to the extent that less than 1% by weight dissolves in 30 minutes at a temperature of 37°C in water adjusted to a pH of 1.2 with hydrochloric acid so that said particles are capable of passing through the stomach in particulate form.

5. A contrast medium composition for nuclear magnetic resonance (NMR) imaging of the gastrointestinal system, comprising an orally or rectally administrable aqueous suspension of finely-divided substantially water-insoluble particles of an NMR paramagnetic contrast agent, said suspension containing wetting and/or suspending agents to maintain said contrast agent particles in a dispersed suspended condition for the administration, said suspension also containing a buffering agent for maintaining the pH of the suspension in a pH range of 6.0 to 8.5 for protecting the insolubility of the contrast agent, said particles being sized below 3 microns diameter and being composed of a metal compound having paramagnetic $T_1$ imaging properties, said particles being insoluble in the suspension to the extent that less than 1% by weight dissolves in 30 minutes at a temperature of 37°C so that said particles are capable of passing through the stomach in particulate form.

6. The method of nuclear magnetic resonance (NMR) imaging of the gastrointestinal system which includes the steps of orally or rectally administering to a human subject the contrast medium composition of claim 1, and obtaining an NMR image of a portion of the gastrointestinal tract in which said paramagnetic

UNITED STATES PATENT AND TRADEMARK OFFICE
CERTIFICATE OF CORRECTION

PATENT NO. : 4,615.879  
DATED : October 7, 1986  
INVENTOR(S) : Val M. Runge & Jeffrey A. Clanton Page 3 of 4

It is certified that error appears in the above-identified patent and that said Letters Patent is hereby corrected as shown below:

compound is present in particulate form.

7. The method of nuclear magnetic resonance (NMR) imaging of the gastrointestinal system which includes the steps of orally or rectally administering to a human subject the contrast medium composition of claim 5 and obtaining an NMR $T_1$-type image of a portion of the gastrointestinal tract in which said paramagnetic compound is present in particulate form.

8. The contrast medium composition of claim 1 in which said water-insoluble metal compound having paramagnetic $T_1$ imaging properties contains a metal selected from the group consisting of gadolinium, chromium, and iron.

9. The contrast medium composition of claim 5 in which said metal compound having paramagnetic $T_1$ imaging properties contains gadolinium.

10. The contrast medium composition of claim 5 in which said metal compound having paramagnetic $T_1$ imaging properties contains chromium.

11. The contrast medium composition of claim 5 in which said metal compound having paramagnetic $T_1$ imaging properties contains iron.

12. The method of nuclear magnetic resonance (NMR) imaging of the gastrointestinal system which includes the steps of orally or rectally administering to a human subject the contrast medium composition of claim 5 in which said metal compound having paramagnetic $T_1$ imaging properties contains gadolinium, and obtaining an NMR $T_1$-type image of a portion of the gastrointestinal tract in which said paramagnetic compound is present

UNITED STATES PATENT AND TRADEMARK OFFICE
CERTIFICATE OF CORRECTION

PATENT NO. : 4,615,879

DATED : October 7, 1986

INVENTOR(S) : Val M. Runge and Jeffrey A. Clanton

It is certified that error appears in the above-identified patent and that said Letters Patent is hereby corrected as shown below:

in particulate form.

13. The method of nuclear magnetic resonance (NMR) imaging of the gastrointestinal system which includes the steps of orally or rectally administering to a human subject the contrast medium composition of claim 5 in which said metal compound having paramagnetic $T_1$ imaging properties contains chromium, and obtaining an NMR $T_1$-type image of a portion of the gastrointestinal tract in which said paramagnetic compound is present in particulate form.

14. The method of nuclear magnetic resonance (NMR) imaging of the gastrointestinal system which includes the steps of orally or rectally administering to a human subject the contrast medium composition of claim 5 in which said metal compound having paramagnetic $T_1$ imaging properties contains iron, and obtaining an NMR $T_1$ image of a portion of the gastrointestinal tract in which said paramagnetic compound is present in particulate form.

Signed and Sealed this

Twenty-seventh Day of January, 1987

Attest:

DONALD J. QUIGG

Attesting Officer     Commissioner of Patents and Trademarks